(12) United States Patent
Rey et al.

(10) Patent No.: US 10,231,671 B2
(45) Date of Patent: Mar. 19, 2019

(54) REDUCTION OF MRI INTERFERENCE FROM THE ELECTROCARDIOGRAM USING LEAD INFORMATION

(71) Applicant: KONINKLIJKE PHILIPS N.V., Eindhoven (NL)

(72) Inventors: Eduardo Mario Rey, Orlando, FL (US); Bernard Lis, Oviedo, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 994 days.

(21) Appl. No.: 14/398,224

(22) PCT Filed: May 15, 2013

(86) PCT No.: PCT/IB2013/053947
§ 371 (c)(1),
(2) Date: Oct. 31, 2014

(87) PCT Pub. No.: WO2013/175349
PCT Pub. Date: Nov. 28, 2013

(65) Prior Publication Data
US 2015/0094561 A1    Apr. 2, 2015

Related U.S. Application Data

(60) Provisional application No. 61/651,173, filed on May 24, 2012.

(51) Int. Cl.
*A61B 5/00* (2006.01)
*A61B 5/0428* (2006.01)
(Continued)

(52) U.S. Cl.
CPC .......... *A61B 5/7203* (2013.01); *A61B 5/0205* (2013.01); *A61B 5/0408* (2013.01);
(Continued)

(58) Field of Classification Search
CPC .................................................. A61B 5/055
See application file for complete search history.

(56) References Cited

U.S. PATENT DOCUMENTS

| 4,537,200 A | 8/1985 | Widrow |
| 4,950,994 A * | 8/1990 | Glover ............... G01R 33/3875 324/318 |

(Continued)

FOREIGN PATENT DOCUMENTS

EP    0470764 A2    2/1992

*Primary Examiner* — James Kish

(57) ABSTRACT

A circuit (32) for use in an magnetic resonance (MR) system to reduce MR interference of a physiological signal S(f) includes a first summing/subtraction node (36), a high pass filter (40), and a second summing/subtraction node (42). The first summing/subtraction node (36) inputs a first signal (34) including radio frequency magnetic interference N(f) and a physiological signal S(f), and a second signal (38) including the physiological signal S(f) and an error signal E(f), and subtractively combines the second signal with the first signal to generate a difference signal N(f)–E(f). The high pass filter (40) filters the difference signal N(f)–E(f) from the first summing/subtraction node. The second summing/subtraction node (42) subtractively combines the first signal S(f)+N(f) (34) and the filtered signal H(f)*[N(f)–E(f)] from the high pass filter, and generates the second signal S(f)+E(f) (38).

20 Claims, 6 Drawing Sheets

Figure 1:
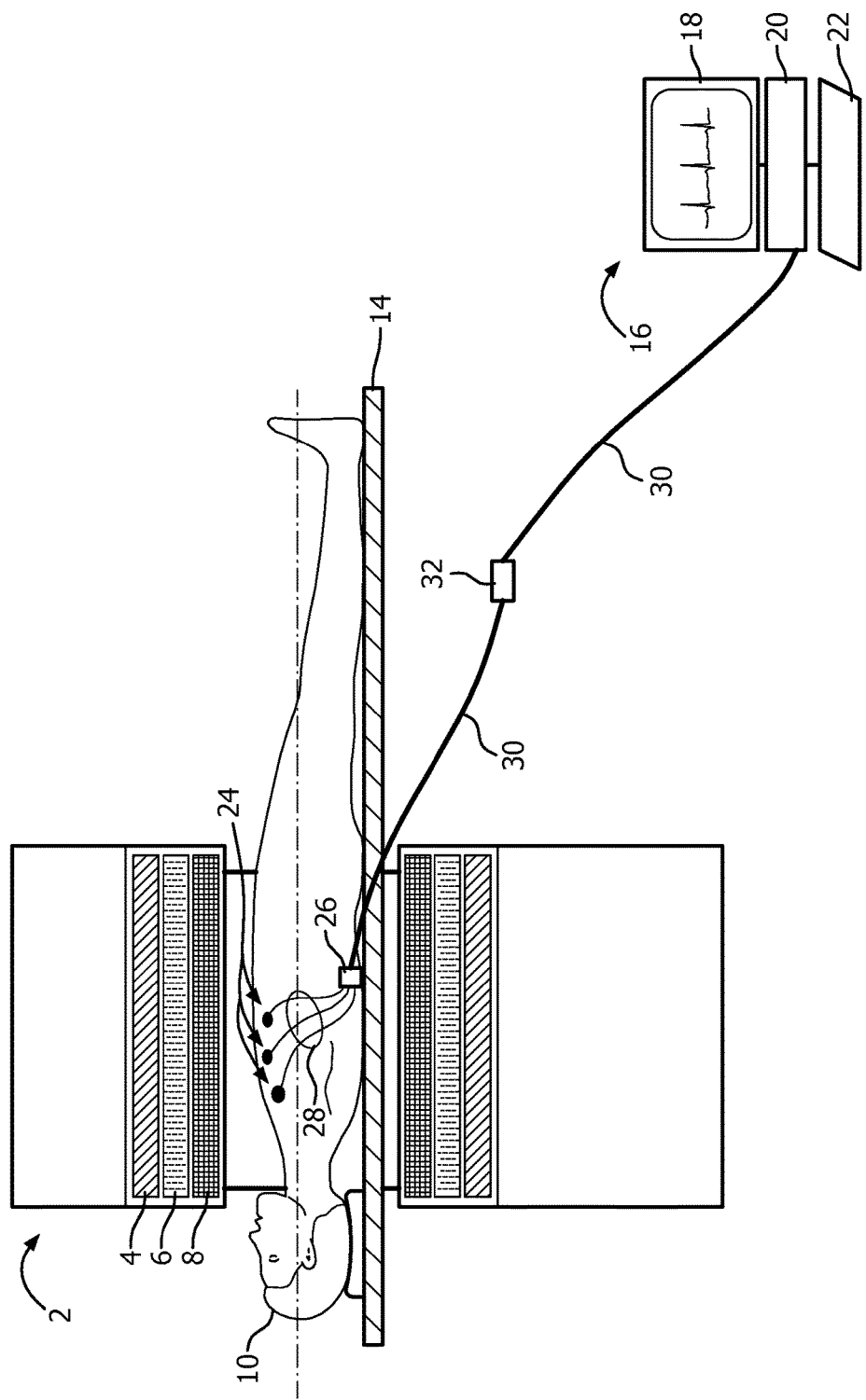

(51) Int. Cl.
   *G01R 33/28* (2006.01)
   *A61B 5/0205* (2006.01)
   *A61B 5/04* (2006.01)
   *A61B 5/0408* (2006.01)
   *A61B 5/055* (2006.01)
   *G01R 33/567* (2006.01)

(52) U.S. Cl.
   CPC ........ *A61B 5/04017* (2013.01); *A61B 5/0428* (2013.01); *A61B 5/7225* (2013.01); *G01R 33/28* (2013.01); *A61B 5/055* (2013.01); *G01R 33/5673* (2013.01)

(56) References Cited

U.S. PATENT DOCUMENTS

| | | | | |
|---|---|---|---|---|
| 4,991,580 A | * | 2/1991 | Moore | A61B 5/0428 600/509 |
| 5,217,010 A | | 6/1993 | Tsitlik et al. | |
| 5,248,943 A | * | 9/1993 | Fox | G01R 33/3415 324/312 |
| 5,436,564 A | * | 7/1995 | Kreger | A61B 5/0424 128/901 |
| 6,052,614 A | | 4/2000 | Morris, Sr. et al. | |
| 6,148,229 A | | 11/2000 | Morris, Sr. et al. | |
| 6,233,548 B1 | * | 5/2001 | Schwartz | H03G 3/3005 704/201 |
| 7,039,455 B1 | | 5/2006 | Brosovich et al. | |
| 7,467,005 B2 | | 12/2008 | Schmid et al. | |
| 8,626,266 B1 | * | 1/2014 | Frank | A61B 5/055 600/413 |
| 2002/0079895 A1 | * | 6/2002 | Roozen | G01R 33/3854 324/318 |
| 2002/0128689 A1 | * | 9/2002 | Connelly | A61N 1/056 607/27 |
| 2004/0097802 A1 | * | 5/2004 | Cohen | A61B 5/04004 600/411 |
| 2004/0135571 A1 | * | 7/2004 | Uutela | A61B 5/04017 324/76.42 |
| 2005/0113666 A1 | | 5/2005 | Bonmassar et al. | |
| 2008/0098097 A1 | | 4/2008 | Motoyama | |
| 2009/0088654 A1 | | 4/2009 | Demharter et al. | |

* cited by examiner

REDUCTION OF MRI INTERFERENCE FROM THE ELECTROCARDIOGRAM USING LEAD INFORMATION

CROSS REFERENCE TO RELATED APPLICATIONS

This application is a national filing of PCT application Serial No. PCT/IB2013/053947, filed May 15, 2013, published as WO 2013/175349 A2 on Nov. 28, 2013, which claims the benefit of U.S. provisional application Ser. No. 61/651,173 filed May 24, 2012, which is incorporated herein by reference.

The following relates generally to medical imaging and patient monitoring. It finds particular application in conjunction with monitoring patients during magnetic resonance imaging and/or spectroscopy procedures, and will be described with particular reference thereto. However, it will be understood that it also finds application in other usage scenarios and is not necessarily limited to the aforementioned application.

In Magnetic Resonance (MR) Imaging, a subject is located in a static magnetic field. Magnetic resonance is excited in tissues of a subject by applying radio frequency (RF) pulses. Gradient magnetic fields or pulses are applied to the subject for spatial encoding, inducing gradient echoes, and the like. As the magnetic resonance in the subject decays, weak RF resonance signals are emitted. The weak RF resonance signals induce current in one or more coils which are used to reconstruct images.

During the imaging process, subjects often are monitored for physiological signs. The physiological monitoring provides monitoring of the vital signs for the subject. The physiological monitor can also be used to correct for motion or other artifacts.

In order to monitor the subject such as for pulse or heart rate, electrodes with lead wires are placed on the skin of the subject. The electrodes measure electrical activity to compute the heart rate or pulse. The lead wires from the electrodes are connected to a physiological device which converts the sensed electrical activity into a waveform signal such as the electrocardiogram signal (ECG). The waveform signal is transmitted along a wire, an optical medium, or wirelessly to a patient monitor or other like device.

Because the wires from the electrodes are electrically conductive, the lead wires and other wires are susceptible to interference currents induced by the gradient field pulses applied to the subject. The induced currents in the electrodes, the electrode lead wires, or a lead wire to the patient monitor, or a combination thereof produces gradient noise interference on the ECG signal. Interference from gradient pulses typically has an amplitude of about ±100 mV but can reach as high as ±10V. An ECG typically has an amplitude of about 300 uV to 5 mV peak-to-peak.

One approach to reducing MR interference is shielding. Heavy shielded cables can be used except for near the electrodes. Shielding the electrodes is difficult and expensive and in most cases prohibitive due to leakage current limitations. Some approaches use fiber optic cable or wireless communication between the device which generates the physiological waveform and the patient monitor. However, interference still occurs at the electrode and the lead wires between the electrodes and the circuitry for converting the electrical ECG signal into light signal, or the like.

Another approach is to use filters. The analog ECG signal can be filtered in the analog domain. Alternatively, digital filtering can be performed after conversion of the analog signal to digital. However, additional firmware resources are needed and the digital signal processing dynamic ranges are often reduced which leads to performance issues and/or increased cost.

Another approach is to determine the theoretical gradient noise interference and use that information to subtract the expected interference from the ECG signal. For example, a connection to a gradient controller of a MR scanner can provide the identity and timing of each gradient field applied to the subject. However, the predicted interference based on the generated sources of interference (e.g. measure of generated gradient fields) and the actual interference on each wire lead or lead cable can vary with electrode placement and the like.

The following discloses a new and improved reduction of MRI interference from the ECG using lead (or electrode) information which addresses the above referenced issues, and others.

In accordance with one aspect, a circuit for use in an magnetic resonance (MR) system to reduce MR interference of a physiological signal S(f) includes a first summing/subtraction node, a high pass filter, and a second summing/subtraction node (42). The first summing/subtraction node inputs a first signal including all interference components generated by the MRI scanner N(f) and a physiological signal S(f), and a second signal including the physiological signal S(f) and an error signal E(f), and subtractively combines the second signal with the first signal to generate a difference signal N(f)−E(f). The high pass filter filters the difference signal N(f)−E(f) from the first summing/subtraction node. The second summing/subtraction node subtractively combines the first signal S(f)+N(f) and the filtered signal H(f)*[N(f)−E(f)] from the high pass filter, and generates the second signal S(f)+E(f).

In accordance with another aspect, a method for use in an MR system to reduce MR interference of a physiological signal S(f) includes inputting (46) a first signal (34) which includes all interference components generated by the MRI scanner N(f) and a physiological signal S(f). The second signal (38) S(f)+E(f) including the physiological signal S(f) and an error signal E(f) is combined subtractively from the first signal S(f)+N(f), and generates a difference signal N(f)−E(f). The difference signal is filtered using a high pass filter. The first signal S(f)+N(f) and the filtered signal H(f)*[N(f)−E(f)] from the high pass filter are combined subtractively, and generate the second signal S(f)+E(f).

In accordance with another aspect, a circuit for use in an magnetic resonance (MR) system to reduce MR interference of a physiological signal S(f) includes a lead, a feed forward path, and a node. The lead carries an input signal including S(f) contaminated with N(f). The feed forward path feeds forward N(f) in a feed forward circuit. The node subtractively combines the input signal and the feed forward signal to generate an output signal.

One advantage is reduced MR gradient interference.

Another advantage resides in removal of interference in hardware before analog-to-digital conversion.

Another advantage resides in using actual interference itself to correct the ECG signal for gradient interference.

Another advantage resides in maintaining the physiological waveform morphology.

Another advantage is a more robust physiological signal quality independent of the scan sequence.

Another advantage is more reliable cardiac gating performance.

Another advantage is not requiring additional electrodes, lead wires, gauss sensors, or the like to capture the interference components generated by the MRI scanner.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 diagrammatically illustrates an embodiment of the interference reduction circuit disposed in a Magnetic Resonance Imaging system.

Figure 2:
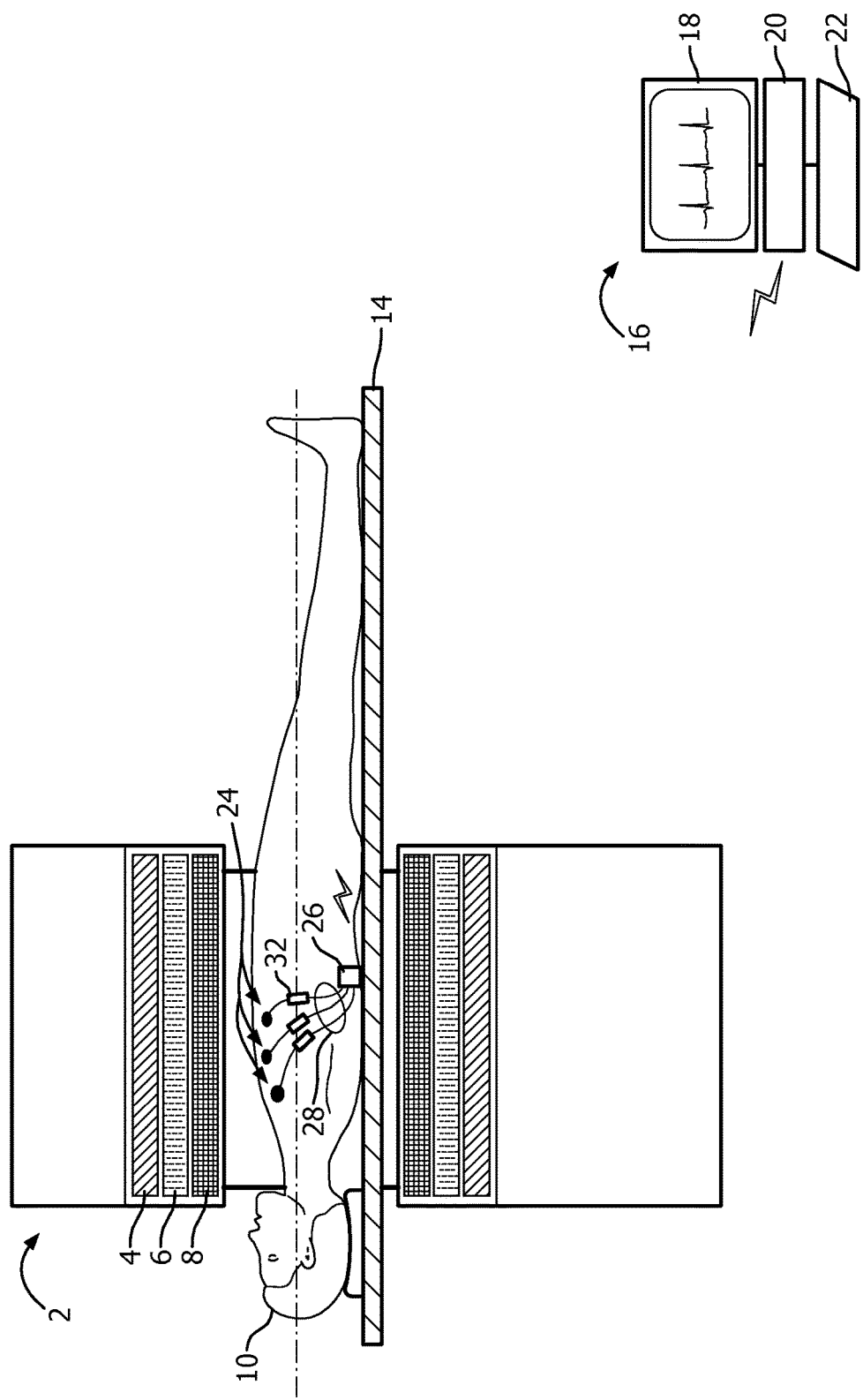
Figure 3:
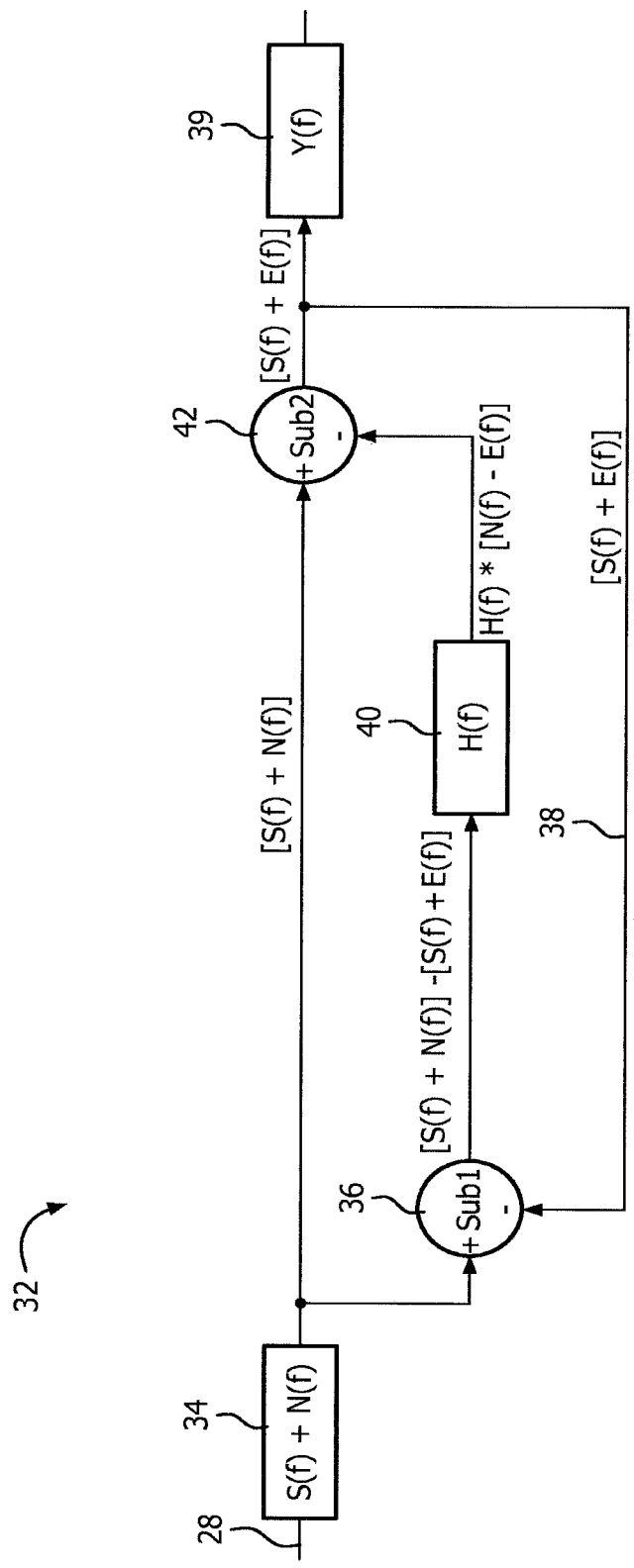

FIG. 2 diagrammatically illustrates another embodiment of the circuit disposed in a Magnetic Resonance Imaging system FIG. 3 diagrammatically illustrates an embodiment of the interference reduction circuit in a block diagram.

Figure 4:
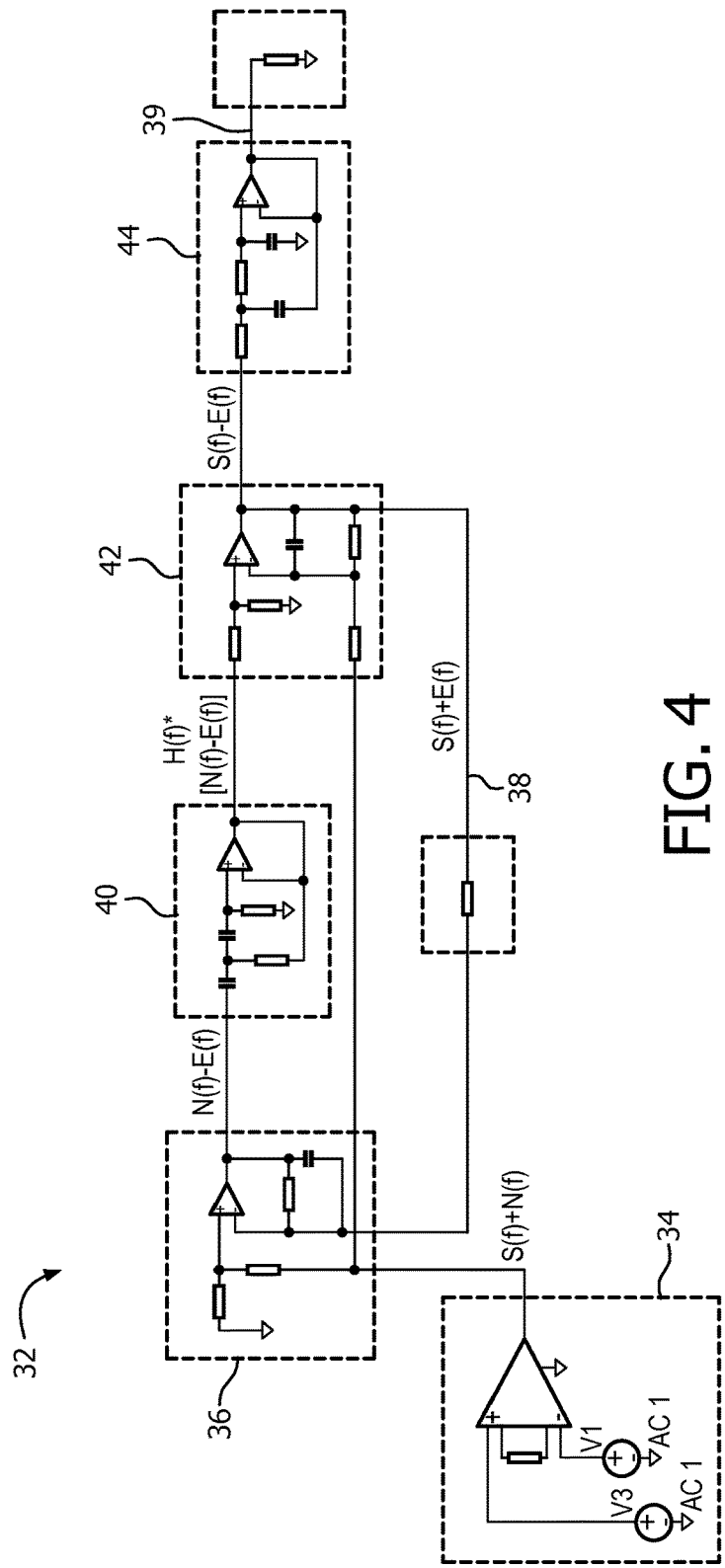

FIG. 4 schematically illustrates an embodiment of the circuit in a circuit diagram.

Figure 5:
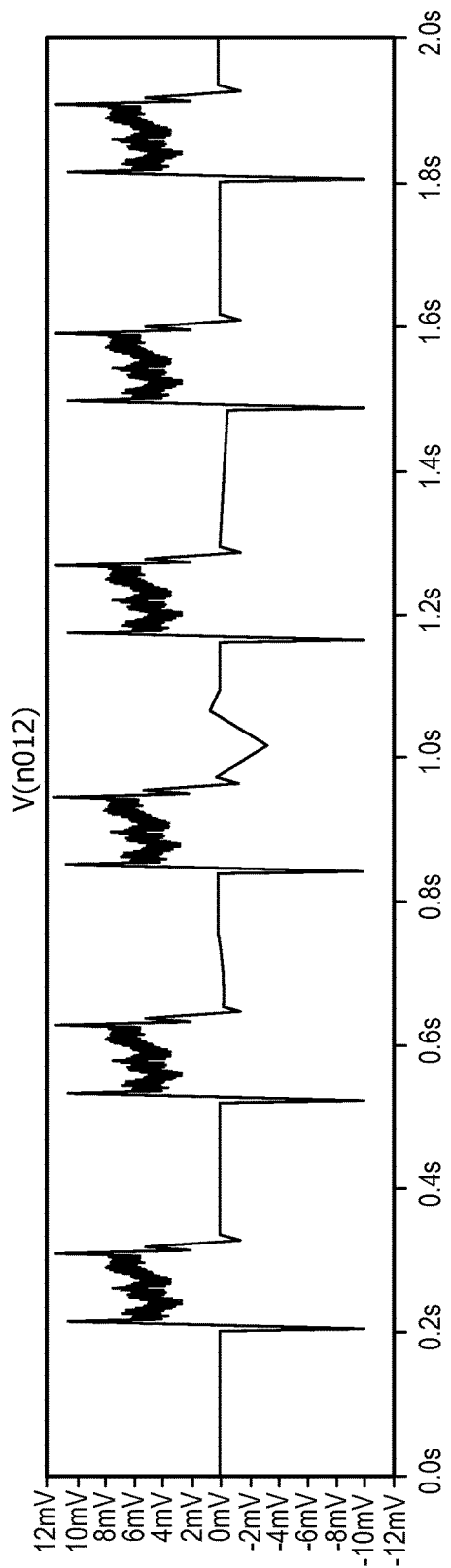

FIG. 5 graphically illustrates an ECG waveform with reduced MR interference.

Figure 6:
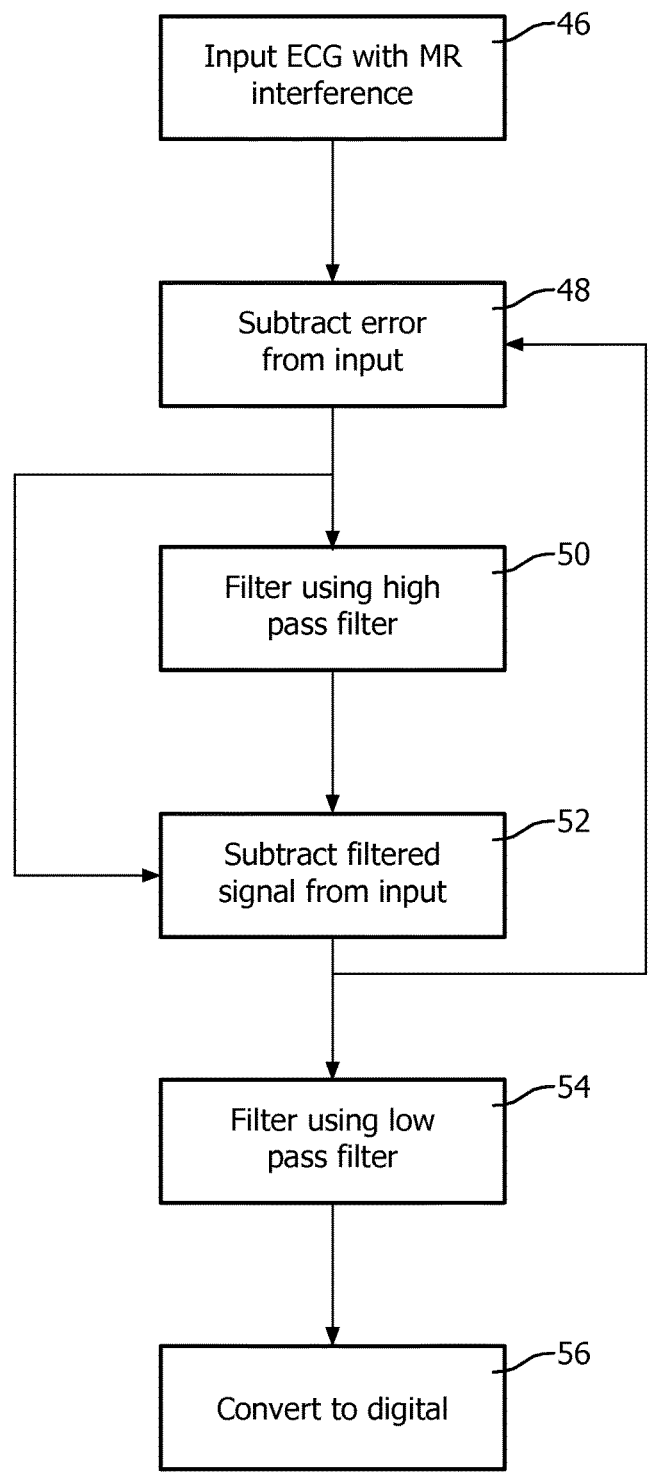

FIG. 6 flowcharts one method of using an embodiment of reducing MR interference on a lead.

With reference to FIG. 1, an embodiment of the interference reduction circuit disposed in a Magnetic Resonance Imaging system is diagrammatically illustrated. The system includes a MR scanner 2 in a cross section view. The scanner 2 includes a main magnet 4, one or more gradient coils 6, and one or more radio frequency (RF) coils 8. The main magnet 4 generates a static or $B_0$ magnetic field. The RF coils generate RF pulses which excite and manipulate magnetic resonance in a subject 10. The one or more gradient coils 6 generate gradient magnetic fields across the static magnetic field spatially encode the induced resonance, induced gradient echoes, and the like. The scanner includes an opening 12 or bore that defines an examination region in which the subject 10 is placed for a spectroscopic and/or imaging examination. The subject is supported by a subject support such as padding 14.

The subject is monitored by a monitoring device 16. The monitoring device 16 includes a display 18, one or more processors 20, and can include at least one input device 22. The display 18 displays the monitored waveforms such as ECG. The one or more processors provide analog to digital signal conversion, filtering, formatting for display of the signal. The monitoring device can include keypad, keyboard, mouse, etc., for entry of information about the subject, and commands to drive the monitoring device. The monitoring device can be connected to a hospital information system (HIS) and the like.

One or more sensors, such as ECG electrodes 24 are attached to the subject to monitor physiological signals from the body surface. The ECG electrodes 24 can be attached with a temporary adhesive that adheres to the skin to sense heart related electrical activity. The electrodes 24 connect to a physiological device 26 by small wires 28 which generates a waveform signal such as an ECG signal. The generated waveform signal is transmitted between the physiological device 26 and the monitoring device 16 via a cable 30. A interference reduction circuit 32 is disposed along the cable 30. The circuit 32 can be disposed at either end or in the middle of the cable. The circuit 32 inputs a signal which includes the waveform signal and interference from the magnetic resonance gradient pulses. The circuit 32 outputs the physiological signal with reduced or removed magnetic interference. The circuit can connect to the physiological device, patient monitor, and/or the cable using standard hardware interfaces such that the circuit can be used with existing devices.

In an alternate embodiment, the circuit 32 can be included in either the physiological device 26 or the monitoring device 20. Incorporating the circuit into one of the devices is advantageous where the signal is transmitted wirelessly or fiber optically. Alternatively the circuit can be included in the cable, a connector, a separate adapter, and/or any combination.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

FIG. 2 diagrammatically illustrates another embodiment of the interference reduction circuit 32 disposed in a Magnetic Resonance Imaging system. The circuit 32 is electrically connected with each of the wire leads 28 from the electrodes 24 affixed to the subject 10 to the physiological device 26. Each wire lead 28 is filtered using the circuit 32 to generate the reduced interference physiological waveform. The physiological device 26 communicates with the patient monitor 16 wirelessly.

FIG. 3 diagrammatically illustrates an embodiment of the interference reduction circuit 32 in a block diagram. The circuit inputs a signal 34 which includes a physiological signal and interference from magnetic resonance such as gradient pulses. The physiological signal is represented by S(f), and the interference or noise of the magnetic resonance represented by N(f). The circuit includes a first summing/subtraction node 36 which receives the input signal 34, S(f)+N(f) and a second or feedback signal 38 which includes the physiological signal and an error component, S(f)+E(f). The first node 36 subtracts the second signal 38 from the input signal 34 which is then fed to a high pass filter 40 such as a Sallen-Key filter. The high pass filter 40 seeks to preserve the interference signal N(f) and minimize an error component E(f). The filtered signal from the high pass filter 40, H(f)*[N(f)−E(f)], is input or fed forward into a second summing/subtraction node 42. The second node 42 subtracts the signal from the high pass filter, H(f)*[N(f)−E(f)] from the original input signal 34, S(f)+N(f), which generates the second signal 38, S(f)+E(f). The second signal 38 includes the physiological signal and the error component which are fed back into the first node 36. The error feedback process minimizes the error signal, E(f), such that the output signal 39 of the circuit is the physiological signal.

The interference reduction circuit can convert the output signal to a digital waveform for further processing, filtering, or display as the physiological signal on the display 18. Prior to the analog-to-digital conversion other options can be included such as low pass filtering, slew-rate limiting, or interpolation stages or any combination thereof. The low pass filter can reduce or eliminate the high frequency component remaining from the subtraction process at the second node 42. The interference reduction circuit can further include an electro-optical transducer, an RF transmitter or the like to convert the output signal 39 to a non-electrical format.

FIG. 4 schematically illustrates an embodiment of the interference reduction circuit 32 in a circuit diagram. The illustrated embodiment includes an ECG filter with an ECG lead input. The ECG lead 28 includes the physiological signal, 34 e.g. ECG signal, and the magnetic resonance interference such as from gradient pulses. The first node 36 includes an operational amplifier and discrete components, and inputs the signal 34 from the lead and subtracts a second signal 38 which includes the ECG signal and an error component. The remaining signal which includes the noise or interference component and the error component is fed into the high pass filter 40. The high pass filter 40 includes an operational amplifier and discrete components. The output signal of the high pass filter is fed into the second node 42. The second node 42 subtracts the output of the high pass filter from the input signal 34 which leaves the physiological signal and the error component and then feeds back the second signal 38 to the first node 36 to minimize the error component E(f). The second node 42 includes an operational amplifier and discrete components. The second signal 38 is fed into an optional low pass filter 44. The output from the low pass filter forms the output 39 from the circuit. The low pass filter includes an operational amplifier and discrete components. The circuit of this embodiment can be implemented with a quad amp package with discrete components.

FIG. 5 graphically illustrates an ECG waveform with reduced MR interference. The overall peak to peak ECG signal is not decreased and the noise of the gradient pulse is reduced. The gradient pulses result in about 2 mV of the noise on the ECG signal. The cause of the remaining noise is the start and finish of the gradient sequences, which are likely due to the head and tail of the high pass filter.

FIG. 6 flowcharts one method of using an embodiment of reducing MR interference on a lead. In a step 46, the signal 34 from a lead wire or electrode wire is input. The signal 34 includes the physiological signal S(f) such as ECG and interference N(f) from magnetic resonance imaging such as from gradient pulses. In an iterative series of steps, beginning with a step 48, the second signal 38 which includes the physiological signal S(f) and the error component E(f) is subtracted from the input signal 34 at the node 36. The subtracted signal S(f)+N(f)−[S(f)+E(f)] is filtered to isolate the interference using the high pass filter 40 in a step 50. The high pass filter preserves the noise or interference N(f) from the magnetic resonance imaging. The filtered signal H(f)*[N(f)−E(f)] is subtracted from the input signal 34 at node 42 in a step 52, and the physiological signal S(f) and the error component E(f) are fed back into the earlier step 48 of subtracting by the node 36 the second signal from the input signal. The feedback and subtracting processes minimize the error component leaving only the physiological signal S(f) such as the ECG signal.

In an optional step 54, the second signal 38 is filtered using the low pass filter 44. The output of the filter can then converted from an analog waveform to digital waveform in a step 56. The analog-to-digital conversion can be optionally included in the circuit 32 or separate. The signal can be transmitted wirelessly, optically, or via wired connection or the like to the patient monitor.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that The invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

The invention claimed is:

1. A circuit for use in an magnetic resonance (MR) system to reduce MR interference of a physiological signal S(f), the circuit comprising:
   a first summing/subtraction node which inputs a first signal including all interference components generated by the MRI scanner N(f) and a physiological signal S(f), and a second signal including the physiological signal S(f) and an error signal E(f), and which subtractively combines the second signal S(f)+FE(f) with the first signal S(f)+N(f) to generate a difference signal N(f)−E(f);
   a high pass filter which filters the difference signal N(f)−E(f) from the first summing/subtraction node to create a filtered signal H(f)*[N(f)−E(f)]; and
   a second summing/subtraction node which subtractively combines the first signal S(f)+N(f) and the filtered signal H(f)*[N(f)−E(f)] from the high pass filter, and generates the second signal S(f)+E(f).

2. The circuit according to claim 1, further including at least one of:
   a low pass filter;
   a slew-rate limit unit; and
   an interpolation unit.

3. The circuit according to claim 1, wherein the first summing/subtraction node, the second summing/subtraction node, and the high pass filter each include an operational amplifier.

4. The circuit according to claim 1, wherein the physiological signal includes an electrocardiogram (ECG) signal.

5. The circuit according to claim 1, further including:
   an analog to digital converter which converts the second signal to a digital signal.

6. The circuit according to claim 1, wherein the high pass filter includes a Sallen-Key filter.

7. The circuit according to claim 1, wherein the interference components N(f) include magnetic field gradient pulse interference.

8. An electrocardiographic system comprising:
   at least one electrode;
   at least one wire, each wire connected to an electrode;
   the circuit of claim 1 connected to the at least one wire to remove the magnetic resonance interference N(f).

9. The system according to claim 8, wherein each at least one wire is connected to a separate circuit.

10. The system according to claim 8, further including:
    at least one patient monitor which receives the physiological signal S(f) with reduced magnetic resonance interference.

11. A method for use in an MR system to reduce MR interference of a physiological signal S(f), the method comprising:
    inputting a first signal which includes all interference components generated by the MRI scanner N(f) and a physiological signal S(f);
    combining subtractively a second signal S(f)+E(f) including the physiological signal S(f) and an error signal E(f) from the first signal S(f)+N(f), and generating a difference signal N(f)−E(f);
    with a high pass filter, filtering the difference signal H(f)−E(f) to generate a filtered signal H(f)*[N(f)−E(f)] in which the interference component N(f) is preserved and the error signal E(f) is minimized;
    combining subtractively first signal S(f)+N(f) and the filtered signal H(f)*[N(f)−E(f)] from the high pass filter, and generates the second signal S(f)+E(f).

12. The method according to claim 11, further including: filtering the second signal using a low pass filter.

13. The method claim 11, wherein the first signal include a physiological signal.

14. The method according to claim 11, further including: converting the second signal from an analog waveform to a digital waveform.

15. The method according to claim 11, wherein the method is performed on each of a plurality of electrocardiogram (ECG) electrode leads.

16. The method according to claim 11, wherein filtering includes slew rate limiting.

17. A non-transitory computer-readable storage medium carrying software which controls one or more electronic data processing devices to perform the method according to claim 11.

18. An electronic data processing device configured to perform the method according to claim 11.

19. A circuit for use in a magnetic resonance (MR) system to reduce MR interference in a physiological signal S(f), the circuit comprising:
    a first summing/subtraction node configured to subtractively combine a first signal including the physiological signal S(f) contaminated with interference components N(f) attributable to a magnetic resonance system and a second signal including the physiological signal S(f) and an error signal E(f) to generate a difference signal N(f)−E(f);
    a filter configured to filter the difference signal N(f)−E(f) from the first summing/subtraction node, the filter being configured to preserve the interference components N(f) and minimize the error component E(f), to generate a filtered difference signal H(f)*[N(f)−E(f)]; and
    a second summing/subtraction node configured to subtractively combine the first signal S(f)+N(f) with the filtered difference signal H(f)*[N(f)−E(f)] from the filter to generate an output signal S(f)+E(f) with the error component E(f) minimized.

20. The circuit of claim 19 wherein the first signal, the second signal, and the output signal are analog and further including one or more processors configured to digitize the output signal and control a display device with the digitized output signal to display the output signal.

* * * * *